US010426394B2

(12) United States Patent
Bulut

(10) Patent No.: US 10,426,394 B2
(45) Date of Patent: Oct. 1, 2019

(54) METHOD AND APPARATUS FOR MONITORING URINATION OF A SUBJECT

(71) Applicant: KONINKLIJKE PHILIPS N.V., Eindhoven (NL)

(72) Inventor: Murtaza Bulut, Eindhoven (NL)

(73) Assignee: KONINKLIJKE PHILIPS N.V., Eindhoven (NL)

(*) Notice: Subject to any disclaimer, the term of this patent is extended or adjusted under 35 U.S.C. 154(b) by 0 days.

(21) Appl. No.: 16/085,313

(22) PCT Filed: Mar. 14, 2017

(86) PCT No.: PCT/EP2017/055882
§ 371 (c)(1),
(2) Date: Sep. 14, 2018

(87) PCT Pub. No.: WO2017/162465
PCT Pub. Date: Sep. 28, 2017

(65) Prior Publication Data
US 2019/0069829 A1    Mar. 7, 2019

(30) Foreign Application Priority Data
Mar. 24, 2016 (EP) ..................................... 16162252

(51) Int. Cl.
*A61B 5/20* (2006.01)
*A61B 5/00* (2006.01)
(Continued)

(52) U.S. Cl.
CPC ................ *A61B 5/202* (2013.01); *A61B 5/01* (2013.01); *A61B 5/1123* (2013.01);
(Continued)

(58) Field of Classification Search
CPC .. A61B 5/20; A61B 5/207; A61B 5/01; A61B 5/202
See application file for complete search history.

(56) References Cited

U.S. PATENT DOCUMENTS 8,204,597 B2    6/2012 Gerber et al.
2005/0038328 A1    2/2005 Stoehrer et al.
(Continued)

FOREIGN PATENT DOCUMENTS

CN    103970271 A    8/2014
JP    2014079506 A    5/2014
(Continued)

OTHER PUBLICATIONS

Inglis-Arkell, Esther, "The Science of Pee Shivers", Oct. 6, 2011, retrieved from the Internet: URL:http://io9.gizmodo.com/5810102/the-science-of-pee-shivers [retrieved on Aug. 31, 2016], pp. 1-3.
(Continued)

*Primary Examiner* — Curtis B Odom

(57) ABSTRACT

There is provided a method of monitoring a subject, the method comprising obtaining measurements of the movements of the subject over time; obtaining measurements of the skin temperature of the subject over time; and processing the obtained measurements of the movements and the obtained measurements of the skin temperature to identify a urination event of the subject. An apparatus for monitoring a subject is also provided.

21 Claims, 7 Drawing Sheets

(51) Int. Cl.
*A61B 5/01* (2006.01)
*A61B 5/11* (2006.01)
*A61B 5/053* (2006.01)
(52) U.S. Cl.
CPC .......... *A61B 5/7282* (2013.01); *A61B 5/0533* (2013.01); *A61B 5/1116* (2013.01)

(56) References Cited

U.S. PATENT DOCUMENTS

2012/0330257 A1* 12/2012 Roe .................. A61F 13/15
604/361
2014/0223406 A1 8/2014 Teller et al.

FOREIGN PATENT DOCUMENTS

JP 2014230679 A 12/2014
WO 2015172246 A1 11/2015

OTHER PUBLICATIONS

Frank, et al., "Comparison of Exact Static and Dynamic Bayesian Context Inference Methods for Activity Recognition", IEEE Explore Digital Library, published 2010 8th IEEE International Conference on Pervasive Computing and Communications Workshops, 7 pages.
Zhou, et al., "Classification of accelerometer wear and non-wear events in seconds for monitoring free-living physical activity", BMJ Open 2015, Downloaded from http://bmjopen.bmj.com/ on Nov. 2, 2015—Published by group.bmj.com, pp. 1-10.

* cited by examiner

METHOD AND APPARATUS FOR MONITORING URINATION OF A SUBJECT

This application is the U.S. National Phase application under 35 U.S.C. § 371 of International Application No. PCT/EP2017/055882, filed on Mar. 14, 2017, which claims the benefit of European Application Serial No. 16162252.7, filed Mar. 24, 2016. These applications are hereby incorporated by reference herein.

TECHNICAL FIELD OF THE INVENTION

The invention relates to a method and apparatus for monitoring a subject, and in particular a method and apparatus for monitoring a subject to identify a urination event of the subject.

BACKGROUND OF THE INVENTION

Urination is characterized by the released of urine from the bladder through the urethra outside the body. In healthy subject, the process of urination is under voluntary control, and occurs in average five (5) to eight (8) times a day. Increased urination frequency and/or duration, among other things, within a subject may be indicative of health disorders.

The monitoring of the urination pattern of a subject such as frequency and duration can be used to assess the health state and the treatment of people. For example there is a need to monitor people suffering from urinary-related diseases and prostate diseases, and people receiving diuretics (so-called water pills). Frequent urination can be a sign of a health issue, like diabetes. Disturbed urination patterns can be sign of stress and anxiety. The progress of other diseases or conditions can also be observed from urination patterns.

Several methods and techniques have been proposed for urination monitoring, such as keeping a urination diary, but these methods and techniques do not provide reliable, automatic, objective or continuous detection and monitoring of urination events. There is therefore a need for an improved method and apparatus for monitoring a subject to identify urination events of the subject.

SUMMARY OF THE INVENTION

According to a first aspect, there is provided a method of monitoring a subject, the method comprising obtaining measurements of the movements of the subject over time; obtaining measurements of the skin temperature of the subject over time; and processing the obtained measurements of the movements and the obtained measurements of the skin temperature to identify a urination event of the subject.

In some embodiments, the step of processing comprises identifying the urination event of the subject as a time period where a level of movement by the subject is below a threshold and the skin temperature decreases.

In some embodiments, the step of processing the obtained measurements comprises processing the obtained measurements of the movements to identify one or more time periods in which the level of movement is below the threshold.

In some embodiments, the step of processing the obtained measurements of the skin temperature comprises processing the obtained measurements to identify time periods in which the skin temperature decreases.

In some embodiments, the step of processing the obtained measurements of the movements further comprises processing the obtained measurements of movements to detect periods of time in which the subject is walking; and identifying the urination event as a time period where the level of movement by the subject is below a threshold and the skin temperature decreases, and where the time period is preceded and followed by a period of time in which the subject is detected to be walking.

In alternative embodiments, the step of processing the obtained measurements of the movements further comprises processing the obtained measurements of movements to detect the posture of the subject over time; and identifying the urination event as a time period where the level of movement by the subject is below a threshold and the skin temperature decreases, and where the subject is in a sitting or standing posture.

In some embodiments, the method further comprises the steps of obtaining measurements of skin conductivity of the subject over time; and processing the obtained measurements of skin conductivity for a time period corresponding to an identified urination event to determine an indication of pain, discomfort, stress, anxiety, emotional fluctuations and/or difficulty for the subject before, during and/or after the urination event.

In some embodiments, the method further comprises the step of analyzing one or more identified urination events to determine one or more characteristics of the urination event or events, the one or more characteristics comprising one or more of the duration of the urination event; the time of the urination event; the frequency with which urination events occur; an indication of pain, discomfort, stress, anxiety, emotional fluctuations and/or difficulty for the subject before, during and/or after the urination event.

According to a second aspect, there is provided a computer program product comprising a computer readable medium having computer readable code embodied therein, the computer readable code being configured such that, on execution by a suitable computer or processor, the computer or processor is caused to perform any of the methods described above.

In some embodiments, the computer or processor obtains the measurements of the skin temperature of the subject from a skin temperature sensor and the computer or processor obtains the measurements of the movements of the subject from a movement sensor.

In some embodiments, the computer or processor is connected or coupled to a movement sensor and a skin temperature sensor.

According to a third aspect, there is provided an apparatus for monitoring a subject, the apparatus comprising a processing unit configured to obtain a movement signal indicative of movements of the subject over time; obtain a skin temperature signal indicative of skin temperature of the subject over time; and process the movement signal and the skin temperature signal to identify a urination event by the subject.

In some embodiments, the apparatus further comprises one or more of a movement sensor configured to measure the movements of the subject over time and output the movement signal; and a skin temperature sensor configured to measure the skin temperature of the subject over time and output the skin temperature signal.

In some embodiments, the apparatus is configured such that the skin temperature sensor measures the skin temperature of the skin on one or the arm, wrist, hand, finger, chest or back of the subject. In some embodiments the apparatus is configured such that the movement sensor is worn on or at one of the arm, wrist, hand, ankle, finger, chest or back of the subject.

In some embodiments, the processing unit is configured to identify the urination event of the subject as a time period where a level of movement by the subject is below a threshold and the skin temperature decreases.

In some embodiments, the processing unit is configured to process the movement signal to identify time periods in which the level of movement is below the threshold.

In some embodiments, the processing unit is configured to process the skin temperature signal to identify time periods in which the skin temperature decreases.

In some embodiments, the processing unit is configured to process the movement signal to detect periods of time in which the subject is walking; and identify the urination event as a time period where a level of movement by the subject is below a threshold and the skin temperature decreases, and where the time period is preceded and followed by a period of time in which the subject is detected to be walking.

In alternative embodiments, the processing unit is further configured to process the obtained measurements of the movements to detect the posture of the subject over time; and identify the urination event as a time period where the level of movement by the subject is below the threshold and the skin temperature decreases, and where the subject is in a sitting or standing posture.

In some embodiments, the apparatus further comprises a skin conductivity sensor configured to measure skin conductivity of the subject over time and output a skin conductivity signal; and wherein the processing unit is configured to process the skin conductivity signal for a time period corresponding to an identified urination event to determine an indication of one or more of pain, discomfort, stress, anxiety, emotional fluctuations and/or difficulty for the subject before, during and/or after the urination event.

BRIEF DESCRIPTION OF THE DRAWINGS

For a better understanding of the invention, and to show more clearly how it may be carried into effect, reference will now be made, by way of example only, to the accompanying drawings, in which.

DETAILED DESCRIPTION OF THE PREFERRED EMBODIMENTS

As noted above, the monitoring of the urination pattern of a subject can be used to assess the health state and the treatment of the subject. Information on the urination patterns or urination events of a subject, including any one or more of the frequency (i.e. how often), the duration, whether there was difficulty starting urination, whether there was urgency to urinate, stop and go patterns during urination, whether the subject had to strain to urinate, pain and/or anxiety before, during or after urination, whether the subject had a feeling of incomplete emptying of the bladder and whether the subject needs to return to urinate shortly after finishing the previous event (e.g. a few minutes), are useful to a doctor or other healthcare professional for diagnosing certain medical conditions and/or tracking the progress and/or treatment of certain medical conditions. Therefore it would be useful to have an apparatus that can monitor a subject and identify urination events by the subject.

Figure 1:
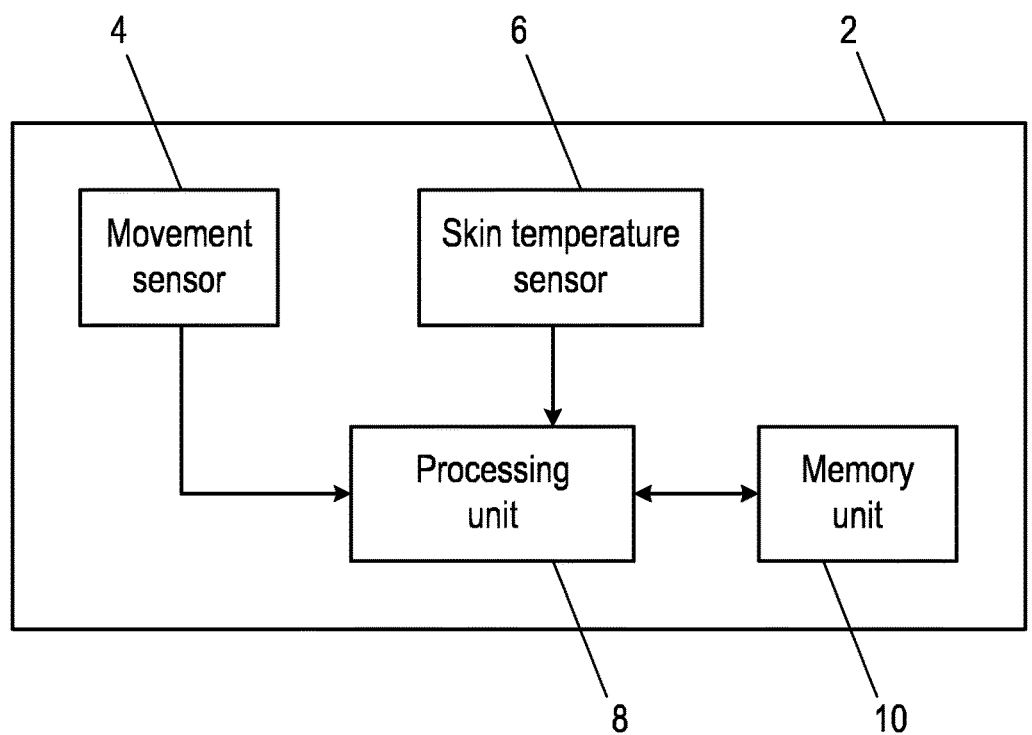
FIG. 1 is a block diagram of an apparatus according to an embodiment of the invention.

An embodiment of an apparatus 2 for monitoring a subject according to the invention is shown in FIG. 1. The apparatus 2 is preferably in a form that can be worn or carried by the subject in a generally unobtrusive manner. For example, the apparatus 2 can be in the form of a watch, wrist band, chest band, or any other type of device that can worn on or around a body part of the subject. In some embodiments the apparatus 2 can be integrated into an item of clothing such as a shirt or jumper. In some embodiments the apparatus 2 can be in a form that is suitable for wearing in or on the skin, for example a plaster or temporary tattoo.

The apparatus 2 comprises a movement sensor 4 that measures the movements or other motion of the subject, or movements or other motion of the part of the body of the subject that the apparatus 2 is worn on or carried by (e.g. the arm of the subject in the case of a wrist-worn or arm-worn apparatus 2). The movement sensor 4 outputs a movement signal indicative of the movements of the subject over time. In some embodiments the movement sensor 4 is an accelerometer that measures accelerations in three dimensions, however in other embodiments the movement sensor 4 can be a gyroscope that measures changes in rotation and orientation or a camera that records images of the subject or the subject's surroundings. In some embodiments, the apparatus 2 can comprise multiple types of movement sensor 4 (e.g. an accelerometer and gyroscope). Those skilled in the art will be aware of other types of movement sensor that can be used in an apparatus 2 according to the invention.

In the case of an accelerometer, the accelerometer can measure the accelerations along three orthogonal axes (e.g. labelled X, Y and Z) and output three signals, each representing the accelerations along a respective one of the axes, or output a single signal that is a composite of the accelerations measured along the three orthogonal axes. The accelerometer 4 (or more generally the movement sensor 4) can operate with any suitable sampling frequency, for example 50 hertz (Hz), i.e. the accelerometer 4 can output an acceleration measurement every $\frac{1}{50}^{th}$ of a second, or for example 10 Hz.

The apparatus 2 also comprises a temperature sensor 6 that is for measuring the temperature of the skin of the subject. The temperature sensor 6 outputs a skin temperature signal indicative of the skin temperature of the subject over time. In some embodiments, the temperature sensor 6 thus comprises a temperature-sensitive element that is placed in contact with an area of the skin of the subject and that provides measurements of the temperature of the surface of the skin. Those skilled in the art will be aware of various types of temperature sensor 6 that can be used in the apparatus 2. Alternatively, the temperature sensor 6 can be an imaging device that is sensitive to infrared light and that images a part of the skin of the subject, and the temperature of the skin of the subject can be determined from the infrared images. In another alternative, rather than measure the temperature of the skin directly (e.g. by using a temperature-sensitive element in contact with the skin), the temperature sensor 6 can measure another physiological characteristic of the subject that is indicative of the skin temperature of the subject, or indicative of changes in skin temperature. In this case, the physiological characteristic is used as a surrogate measure for skin temperature. For example, the temperature sensor 6 can be a photoplethysmograph (PPG) sensor that measures characteristics of the blood flow beneath the skin, and characteristics of the pulse or signal amplitude can be used as the surrogate skin temperature measurement. Suitable characteristics include the signal amplitude, peak-to-peak amplitude, beat-to-beat amplitude fluctuation. Each of these characteristics vary with changes in skin temperature. As with the movement sensor 4, the temperature sensor 6 can operate with any suitable sampling frequency, for example 50 Hz or 10 Hz. In some embodiments, the temperature sensor 6 has a measurement resolution of 0.02 degree Celsius (° C.).

The measurements of the movements (the movement signal) and the measurements of the skin temperature (the skin temperature signal) are provided to a processing unit 8 in the apparatus 2. The processing unit 8 processes the measurements/signals to identify a urination event of the subject, as described in more detail below. The processing unit 8 also controls the operation of the apparatus 2, for example controlling the initiation of the collection of measurements by the movement sensor 4 and/or skin temperature sensor 6, and/or other functions and operations of the apparatus 2. The processing unit 8 can be implemented in numerous ways, with software and/or hardware, to perform the various functions required. The processing unit 8 may comprise one or more microprocessors that may be programmed using software to perform the required functions. The processing unit 8 may be implemented as a combination of dedicated hardware to perform some functions and a processor (e.g., one or more programmed microprocessors and associated circuitry) to perform other functions. Examples of controller components that may be employed in various embodiments of the present disclosure include, but are not limited to, conventional microprocessors, application specific integrated circuits (ASICs), and field-programmable gate arrays (FPGAs).

In various implementations, the processing unit 8 may be associated with one or more storage media, shown as memory unit 10 in FIG. 1. The memory unit 10 can be part of the processing unit 8, or it can be a separate component in the apparatus 2 that is connected to the processing unit 8. The memory unit 10 can comprise any suitable or desired type of volatile or non-volatile computer memory such as RAM, PROM, EPROM, and EEPROM. The memory unit 10 can be used for storing program code that can be executed by the processing unit 8 to perform the method described herein. The memory unit 10 can also be used to store signals or measurements from the movement sensor 4 and/or skin temperature sensor 6, and/or information relating to urination events identified by the processing unit 8.

In some embodiments, the apparatus 2, including the movement sensor 4 and skin temperature sensor 6, can be in a form that can be worn on or near the wrist, arm, hand or finger(s) of the subject. For example the apparatus 2 can be in the form of a watch or wrist band or strap. In these embodiments, the skin temperature sensor 6 measures the skin temperature on or near the wrist, or on the arm, hand or finger(s) of the subject. Alternatively, the apparatus 2, including the movement sensor 4 and skin temperature sensor 6, can be in a form that can be worn on the chest or back of the subject. For example the apparatus 2 can be in the form of a patch that can be adhered or otherwise fixed to the subject. In these embodiments, the skin temperature sensor 6 measures the skin temperature on the chest or back of the subject.

In some embodiments the movement sensor 4 and skin temperature sensor 6 are part of the same device or housing as the processing unit 8, but in other embodiments the movement sensor 4 and skin temperature sensor 6 are in a separate device or housing to the processing unit 8. Where the movement sensor 4 and skin temperature sensor 6 are provided in a separate device or housing to the processing unit 8, appropriate circuitry or components can be provided to enable the measurement signals to be sent from the movement sensor 4 and skin temperature sensor 6 to the processing unit 8. For example where the movement sensor 4 and skin temperature sensor 6 are worn on or near the wrist of the subject, the processing unit 8 can be part of a smartphone or other electronic device that the subject carries in their pocket or wears on their chest, in which case the measurements from the movement sensor 4 and skin temperature sensor 6 can be sent wirelessly to the processing unit 8 in the smartphone or other device so that the urination events can be identified.

In some embodiments the processing unit 8 can receive the measurements/signals directly from the movement sensor 4 and skin temperature sensor 6 and the processing unit 8 can process these measurements in real-time or near real-time in order to identify urination events of the subject. In other embodiments (including embodiments where the movement sensor 4 and skin temperature sensor 6 are separate from the processing unit 8), the measurements from the movement sensor 4 and skin temperature sensor 6 can be stored in memory unit 10 and the processing unit 8 can retrieve and analyze the previously-obtained sensor measurements from the memory unit 10 when urination events of the subject are to be identified.

As noted above, in some embodiments the processing unit 8 may be part of a smart phone or other general purpose computing device that can be connected to or otherwise receive a measurement signal from movement sensor 4 and skin temperature sensor 6, but in other embodiments the apparatus 2 can be an apparatus that is dedicated to the purpose of identifying urination events of a subject. In embodiments where the processing unit 8 is part of a smart phone or other general purpose computing device, the movement sensor 4 could be the accelerometer, gyroscope and/or other type of movement sensor typically found in such a smart phone. The skin temperature sensor 6 could also be integrated into the smart phone or computing device, or provided separate to the smart phone or computing device so that it can provide skin temperature signals/measurements to the smart phone/computing device for processing and analysis (for example via a wired or wireless connection).

It will be appreciated that FIG. 1 only shows the components required to illustrate this aspect of the invention, and in a practical implementation the apparatus 2 will comprise additional components to those shown. For example, the apparatus 2 may comprise a battery or other power supply for powering the apparatus 2, a communication module for enabling the information on identified urination events to be communicated to a base unit for the apparatus 2 or a remote computer, and/or one or more user interface components that allow the subject or another user to interact and control the apparatus 2. As an example, the one or more user interface components could comprise a switch, a button or other control means for activating and deactivating the apparatus 2 and/or urination event identification process. The user interface components can also or alternatively comprise a display or other visual indicator for providing information to the subject and/or other user about the operation of the apparatus 2, including displaying information on identified urination events.

In some embodiments of the invention, which are described in more detail below with reference to FIG. 7, the apparatus 2 further comprises a skin conductivity sensor for measuring the conductivity of the skin of the subject. The skin conductivity sensor can comprise two or more electrodes that are for contacting the skin of the subject and the voltage or current through the skin between the electrodes can be measured in order to determine the conductivity. However, those skilled in the art will be aware of other types of skin conductivity sensor that can be used in the apparatus 2. The skin conductivity sensor is connected to the processing unit 8 and provides measurements of the conductivity of the skin of the subject (e.g. in the form of a skin conductivity signal). The skin conductivity sensor can operate with any suitable sampling frequency, for example 50 Hz or 10 Hz.

Figure 2:
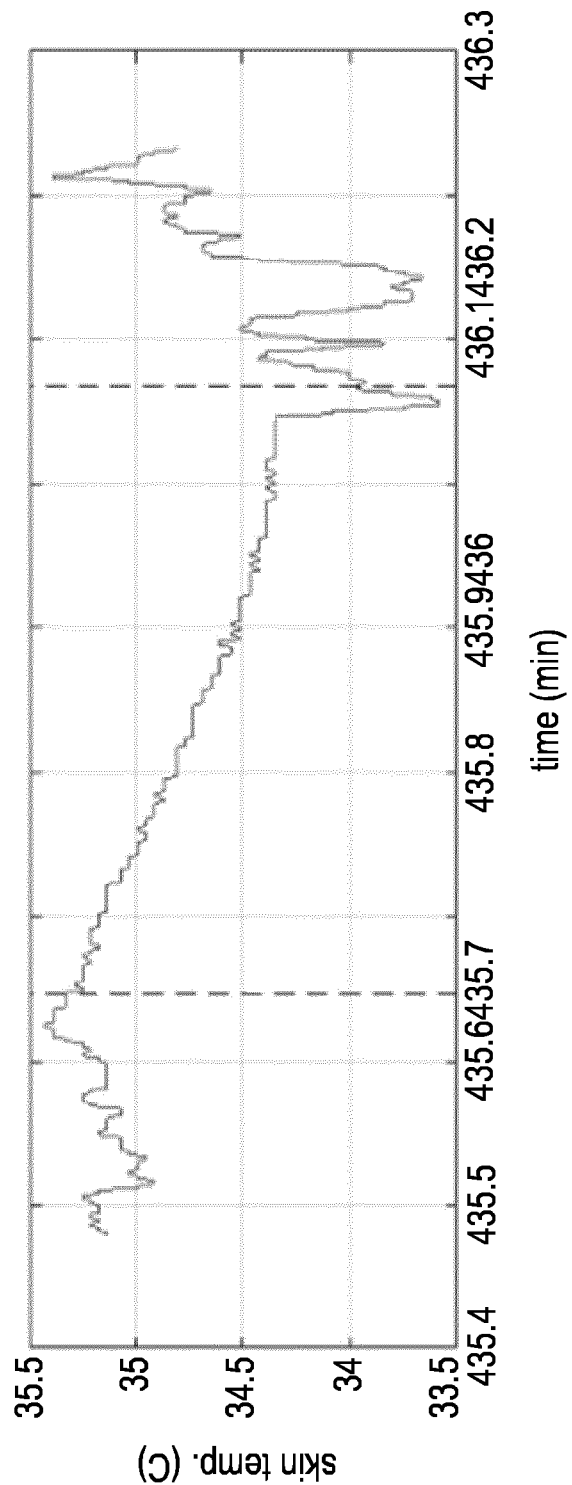
FIG. 2 is a graph illustrating changes in skin temperature during and around a urination event.

The identification of urination events of a subject according to the invention is based on the realization that the skin temperature of a subject decreases during a urination event. The graph in FIG. 2 shows measurements of skin temperature over a time period that includes a urination event. The urination event starts at around 435.65 minutes and ends at around 436.07 minutes, and it can be seen that the skin temperature decreases at a reasonably constant rate during the urination event. It has been found that the decrease in skin temperature during a urination event is on average 0.1-0.2° C., but it can be as high as 1° C. In the example shown in FIG. 2, the skin temperature decreases by around 0.9° C. across the urination event. More generally, for cases where the skin temperature is lower than the core body temperature (which is the case except for extreme conditions), urinating causes a drop/decrease in skin temperature. Regular skin temperature can be 33° C., and regular core body temperature is 37° C. The temperature of the urine inside the body is close to the core body temperature, i.e. 37° C. When this hot fluid (urine) is removed from the body, the skin temperature drops.

However, observing changes in skin temperature alone does not provide a sufficiently high reliability rate (since skin temperature can change for reasons other than just urination events), and therefore the invention provides that measurements of the movements of the subject are analyzed to identify periods of time that might correspond to urination events (i.e. candidate urination events) and then the change in skin temperature during these candidate urination events is evaluated to determine if the candidate urination event is a urination event.

Figure 3:
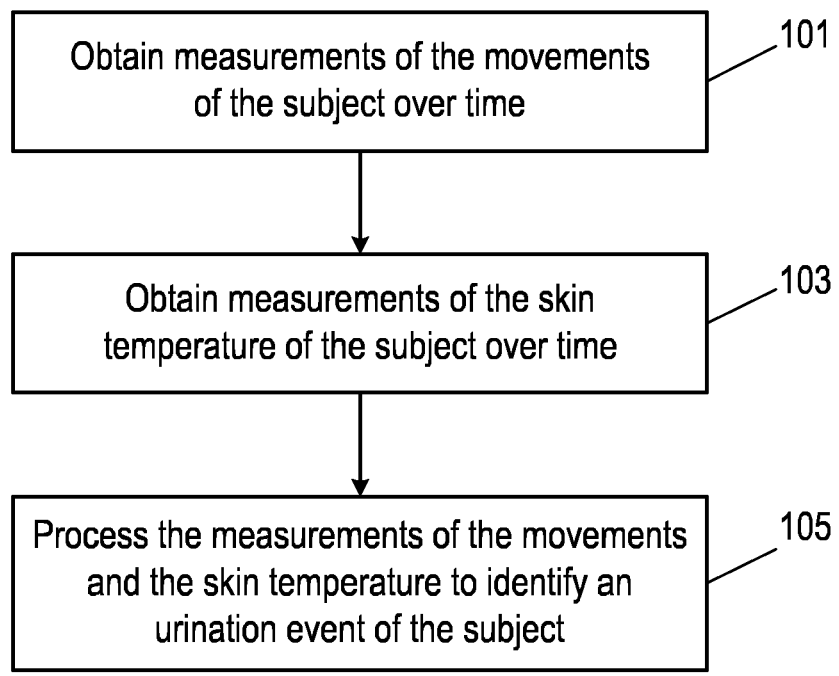
FIG. 3 is a flow chart illustrating a method according to an embodiment of the invention.

A method of monitoring a subject to identify urination events is shown in the flow chart of FIG. 3. In step 101 measurements of the movements of the subject over time are obtained and in step 103 measurements of the skin temperature of the subject over time are obtained. It will be appreciated that the measurements of the movements and the measurements of the skin temperature are obtained over corresponding (i.e. overlapping) time periods. Steps 101 and 103 can comprise obtaining the measurements directly using the movement sensor 4 and the skin temperature sensor 6, or retrieving measurements made using the movement sensor 4 and the skin temperature sensor 6 from the memory unit 10. It will be appreciated that references in the following explanation of the invention to the measurements of the movements and measurements of the skin temperature include reference to the movement signal and the skin temperature signal respectively.

The measurements of the movements and the measurements of the skin temperature are then processed to identify a urination event of the subject (step 105). Step 105 can be performed by processing unit 8.

An exemplary algorithm that can be used to identify urination events from movement measurements and skin temperature measurements in step 105 is described below with reference to FIGS. 4-6.

Figure 4:
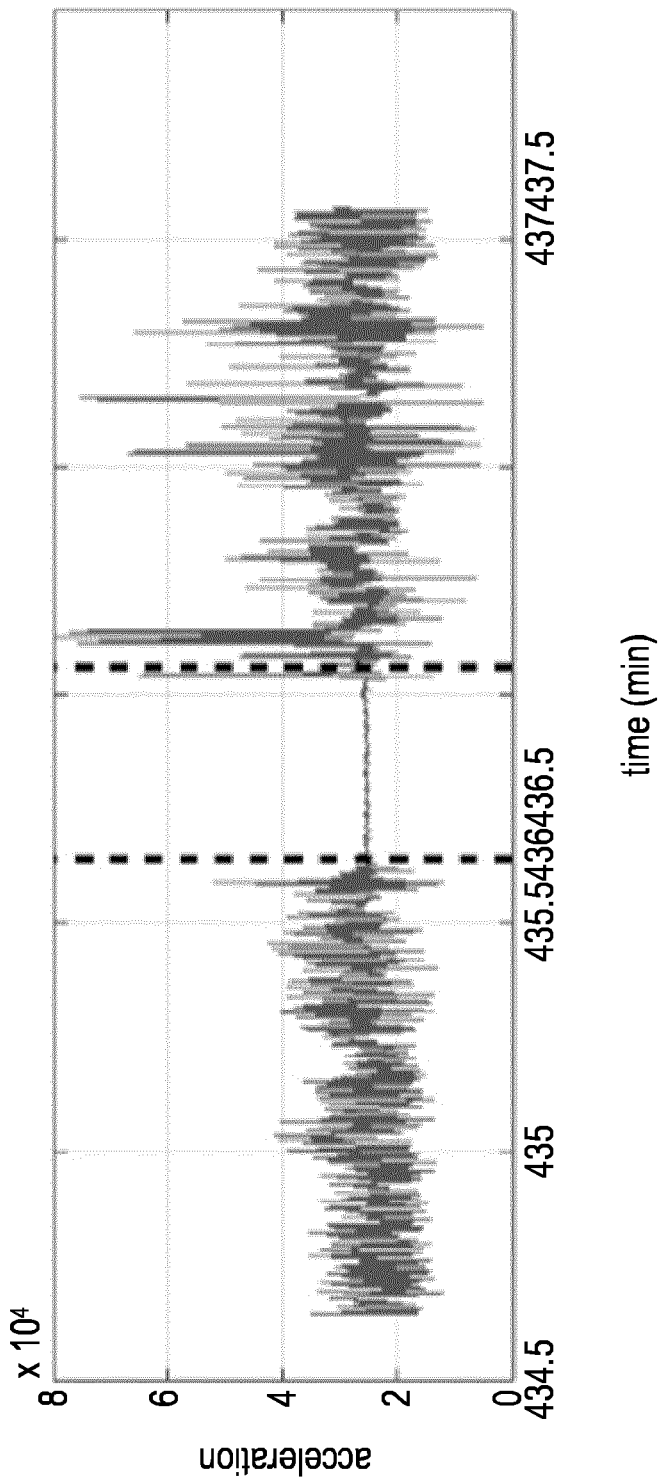
FIG. 4 is a graph illustrating an exemplary measurement signal from an accelerometer.

The graph in FIG. 4 illustrates an exemplary measurement signal from an accelerometer 4 that illustrates the accelerations before, during and after a urination event. The urination event occurred approximately between 435.6 minutes and 436.1 minutes, and it can be seen that there is little acceleration or activity by the subject during this time. It will be appreciated that a measurement signal exhibiting similar characteristics would be obtained from other types of movement sensors.

Since a urination event (i.e. the act of urinating) does not involve much movement by the subject (as shown in FIG. 4), the movement measurements can be processed to identify time periods in which there is low activity/movement by the subject. Thus, in some embodiments the movement measurements are processed to identify time periods in which the level of movement is below a threshold for the duration of the time period. The level of movement for a particular time instant can be given by the magnitude of the movement in the movement measurements (e.g. the magnitude of the acceleration in the case of acceleration measurements), and a time period where there is low activity/movement can be identified where the magnitude of the movement is below the threshold for the duration of the time period. Alternatively the level of movement can be given by an activity count, movement count or energy that can be derived from the movement measurements, and a time period where there is low activity/movement can be identified where the activity count, movement count or energy is below the threshold. It will be appreciated that an activity count, movement count or energy can be derived for a small amount of time (e.g. 1 second), and thus a time period where there is low activity/movement can be identified where the activity count, movement count or energy are below the threshold for the duration of the time period. Those skilled in the art will be aware of various techniques for determining a level of movement from movement measurements, including from the magnitude, an activity count, movement count or energy.

Figure 5:
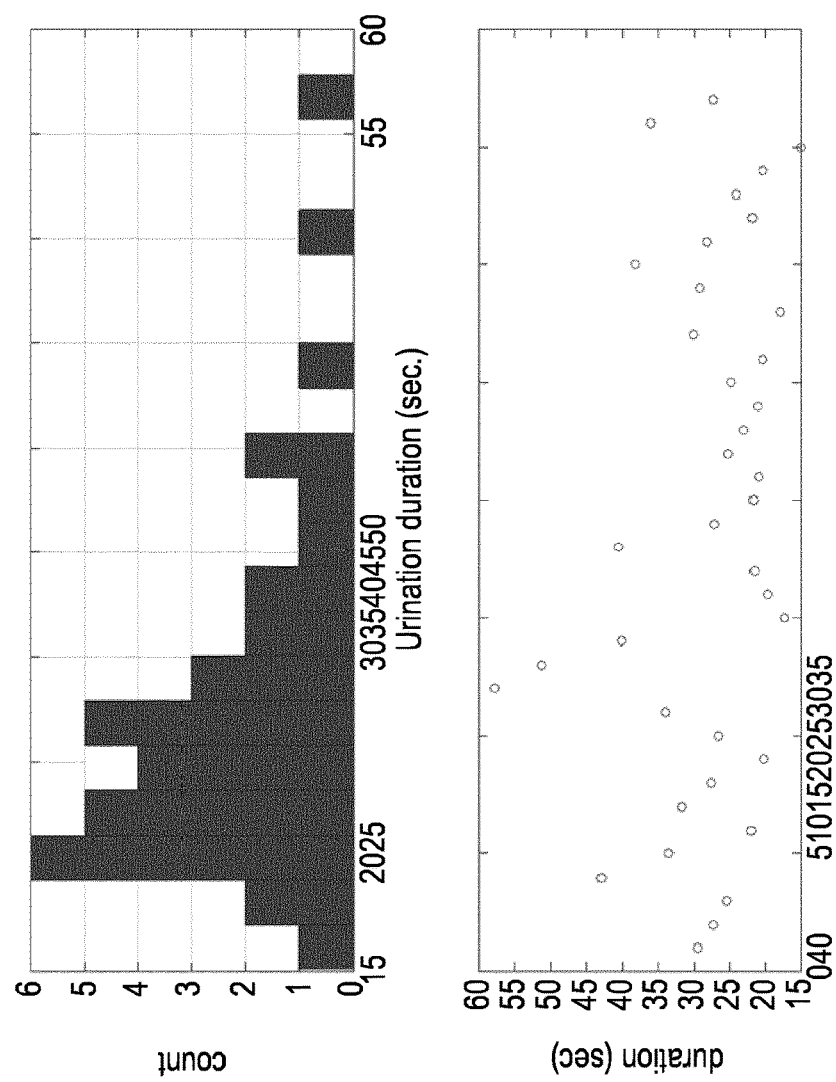
FIG. 5 is a pair of graphs illustrating the distribution of the duration of a number of urination events.

In addition, a urination event is typically quite a short event (i.e. not lasting more than say, 1 minute in length), which is shown in FIG. 5. The bottom graph in FIG. 5 shows the duration in seconds of a number of known urination events and it can be seen that the events range in duration from 15 to 60 seconds. The data from the bottom graph in FIG. 5 is shown in a distribution graph in the top graph of FIG. 5, and it can be seen that most urination events have a duration of 20-30 seconds, with the average urination duration being around 28 seconds.

Therefore, in some embodiments, the movement measurements can be processed to identify time periods of low activity/movement (i.e. where the level of movement is below the threshold) having a length that could correspond to a urination event. As such, in some embodiments, periods of low activity/movement that are much longer than a possible urination event (e.g. greater than 2 minutes) can be discarded at this stage of the algorithm. In other embodiments, only periods of low activity/movement that are within an acceptable range (e.g. between 5 and 60 seconds) are identified at this stage of the algorithm.

Furthermore, a urination event is normally preceded by the subject walking or otherwise moving to the toilet, and followed by the subject walking or otherwise moving away from the toilet. Thus, the periods of low activity/movement identified in this part of the algorithm should also be preceded and followed by periods of higher activity/movement (i.e. a level of movement/activity above the threshold). These higher activity periods can also be seen in the measurements in FIG. 4. It will be appreciated that the low level of movement/low activity and high level of movement/high activity may have respective thresholds, e.g. a low activity threshold below which the activity level (level of movement) is low, and a high activity threshold (that is higher than the low activity threshold) above which the activity level (level of movement) is high.

In some embodiments, the movement measurements can be processed to detect or identify periods of time of a required duration (e.g. up to 2 minutes, between 5 and 60 seconds, etc.) in which there is low activity (low level of movement), and then the measurements either side of the detected period can be analyzed to determine if they correspond to high activity or walking. Any low activity period (of the required duration) in the movement measurements that is preceded and followed by high activity periods are identified as candidate urination events (i.e. the low activity period may correspond to a urination event).

In alternative embodiments, the movement measurements can be analyzed to detect high-low-high activity/movement/ energy patterns using short time windows-based analysis. The window could, for example, be 3 minutes in length since that would cover the urination event and walking to the toilet prior to the event and walking away from the toilet after the event. Any window that shows a high activity low activity high activity pattern (where the high activity can be where the activity level (level of movement) is above a threshold and low activity can be where the activity level (level of movement) is below the or a respective threshold) may correspond to a urination event.

Figure 6:
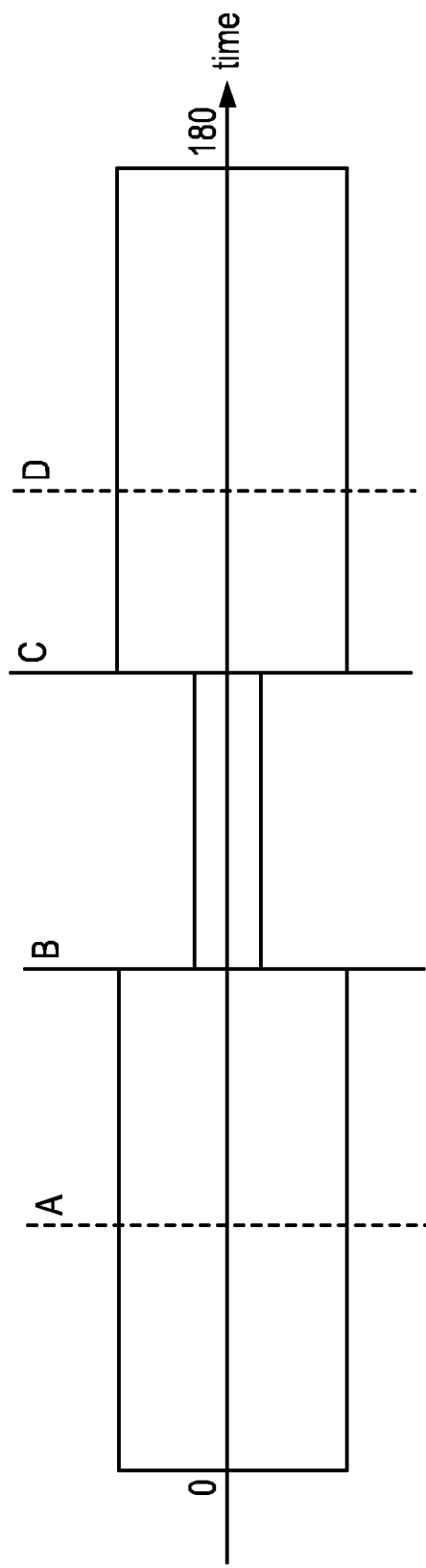
FIG. 6 is an illustration of the segmentation of measurements from a movement sensor.

FIG. 6 illustrates an exemplary windowing or segmentation of movement measurements using a 3 minute window with a low activity portion (between lines B and C) sandwiched between two higher activity portions (between lines A and B and C and D). In window-based processing, the window is applied to the start of the movement measurements (e.g. the first 3 minutes of measurements), and the measurements inside the window are analyzed to determine if the pattern shown in FIG. 6 is satisfied. The window can then be shifted along the movement measurement signal, for example shifted by 1 second, and the measurements inside the shifted window analyzed, and so on.

In view of the information on the duration or urination events shown in FIG. 5, any window of movement measurements that satisfies the high activity low activity high activity pattern shown in FIG. 6, and where the low activity portion is of a required duration (e.g. no longer than 2 minutes, or between 5 and 60 seconds, etc.) is considered to be a candidate urination event.

As noted above, it will be appreciated that where the movement measurements are acceleration measurements, low activity and high activity (low level of movement and high level of movement respectively) can correspond to the value or magnitude of the acceleration being below or above a threshold respectively. Alternatively, the acceleration measurements can be processed to determine an energy or activity level signal, and the energy or activity level compared to an appropriate threshold to identify the required high and low activity periods.

At this stage, it is not clear from the movement measurements whether the candidate urination events actually correspond to urination events. For example, the low activity period between B and C in FIG. 5 and the low activity period between 435.6 minutes and 436.1 minutes in FIG. 4 could simply be a time period where the subject was standing still or sat down.

Therefore, the measurements of the skin temperature can be used to determine if the candidate urination events identified above correspond to an actual urination event. In some embodiments, the skin temperature measurements for time periods corresponding to the time periods of candidate urination events can be analyzed to determine if the skin temperature decreases, and if so, the candidate urination event can be classified as a urination event. If the candidate urination event does not have a corresponding decrease in skin temperature the candidate urination event can be discarded. In some embodiments, the decrease in the skin temperature corresponding to a urination event may be required to be in a predetermined range, e.g. between 0.1° C. and 1° C. In some embodiments, the decrease in the skin temperature corresponding to a urination event may be required to be a gradual decrease in the skin temperature across the whole urination period, rather than simply any drop in skin temperature during the candidate urination period.

Thus, by making use of relative changes in movement measurements and skin temperature measurements, it is possible to detect urination events of the subject.

It will be appreciated that in alternative implementations of step 105, candidate urination events can be identified from the skin temperature measurements (e.g. periods up to a required duration (e.g. up to 2 minutes or between 5 and 60 seconds) where the skin temperature decreases by up to (1° C.)), and the movement measurements can be analyzed to determine whether any of the candidate urination events are actual urination events (e.g. by determining if the decrease in skin temperature coincides with a period of low activity, and optionally determining if the period of low activity is preceded or followed by periods of high activity).

Once one or more urination events are identified in the measurements, one or more characteristics of the urination event(s) can be determined. For example, each identified urination event can be analyzed to determine the duration, where the duration is given by the duration of the skin temperature decrease and/or the duration of the low activity period. As another example, the frequency of urination events can be determined once a number of urination events have been identified. The time of the urination event can be determined, and the time at which different urination events occurred compared. It is also possible to obtain information on whether the subject is having difficulty urinating by analyzing the movement measurements in the B-C period, for example analyzing the signal energy to provide an indication of motion, which can be associated with difficulty or pain during the urination event. Information on stop-and-go patterns can be determined from the movement and skin temperature measurements. The characteristics of multiple urination events can be compared or evaluated to determine whether the characteristic is changing over time. Such changes can be indicative of improvements or worsening of a medical condition suffered by the subject.

In addition to the above processing and analysis, there are several optional steps that could be performed (either individually or in combination) to improve the accuracy of the urination event detection.

In a first optional step, a (candidate) urination event can only be detected where the subject is walking before and after the low activity period. As noted above, a urination event is typically preceded and followed by walking events. Although in the processing set out above it is necessary to determine if there are high activity periods before and after the low activity period corresponding to the urination event, in this optional step, the movement measurements are further analyzed to determine if the subject is walking during those high activity periods. If it is determined that the subject is not walking during one or both of those high activity periods, then the candidate urination event can be discarded. Those skilled in the art will be aware of various techniques for detecting if the subject is walking from movement sensor measurements (particularly accelerometer measurements).

In a second optional step, a (candidate) urination event can only be detected where the subject is in a sitting or standing posture for the duration of the (candidate) urination event. Thus, in this optional step, the movement measurements are further analyzed to determine if the subject is sitting or standing during the low activity period. If it is determined that the subject is not sitting or standing during the low activity period, then the candidate urination event can be discarded. Those skilled in the art will be aware of various techniques for detecting the posture of the subject from movement sensor measurements (particularly accelerometer measurements).

In a third optional step, further analysis of the movement measurements can be performed to detect other movements that are typical of visits to the toilet, such as opening and closing doors, washing hands and removing clothing. If the analysis of the movement measurements indicates that such movements have not occurred around the candidate urination event after the first walking/high activity period and before the second walking/high activity period, then the candidate urination event can be discarded. Those skilled in the art will be aware of various techniques for detecting particular movements or types of movements from movement sensor measurements (particularly accelerometer measurements).

In this third optional step, it will be appreciated that the analysis is effectively aiming to identify a portion of the movement measurements having five distinctive parts, the low activity and walking periods described above (which each exhibit a generally regular movement pattern), and two high activity parts between the first walking period and the low activity period and the low activity period and the second walking period respectively that correspond to the other movements that are typical of visits to the toilet (and which are generally more irregular than activities such as walking).

As noted above, in some embodiments of the invention, the apparatus 2 further comprises a skin conductivity sensor for measuring the conductivity of the skin of the subject. Thus, in some embodiments the skin conductivity measurements can be used in combination with the movement measurements and the skin temperature measurements to identify urination events of the subject.

Figure 7:
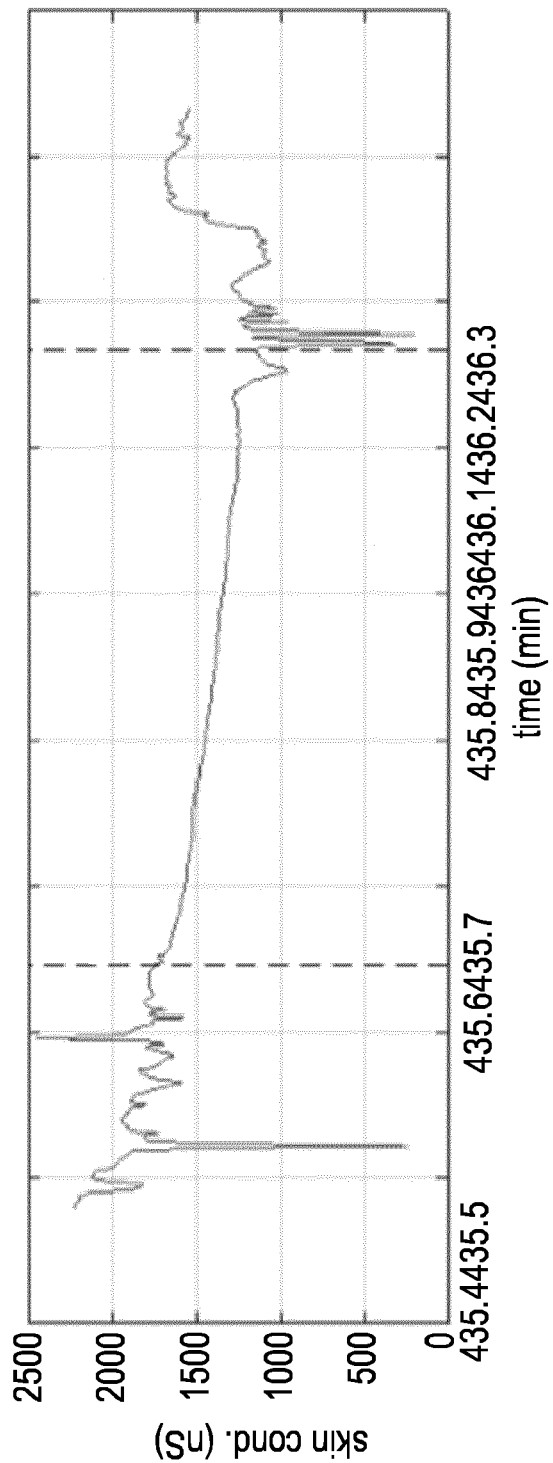
FIG. 7 is a graph illustrating the changes in skin conductance during and around a urination event.

In particular, as shown in FIG. 7, during urination between 435.6 minutes and 436.1 minutes, the skin conductance level decreases, and this decrease is generally smooth. Thus, in some embodiments, the skin conductivity measurements for time periods corresponding to candidate urination events can be evaluated to determine if the skin conductivity decreases during the urination event. If the decrease in skin conductivity is not present, then the candidate urination event can be discarded. In some embodiments, the decrease in the skin conductivity corresponding to a urination event may be required to be in a predetermined range, e.g. between 10 nS to 1000 nS, although in some embodiments the upper and lower bound of the predetermined range can be different. In some embodiments, the decrease in the skin conductivity corresponding to a urination event may be required to be a gradual decrease in the skin conductivity across the whole urination period, rather than simply any drop in skin conductivity during the candidate urination period.

In further embodiments, since skin conductivity is a parameter that is sensitive to pain, discomfort, stress, anxiety and emotional fluctuations of the subject, the measurements of skin conductivity can be analyzed to determine if the subject is experiencing pain, discomfort, stress, anxiety or emotional fluctuations before, during and/or after the urination event. Thus, the skin conductivity measurements corresponding to an identified urination event can be analyzed to determine the skin conductivity response, and this response can be used to provide an indication of the pain, discomfort, stress, anxiety, difficulty or emotional fluctuations of the subject using techniques known in the art (for example techniques that evaluate the number of peaks, the amplitude of the peaks, and/or the peak rise time in the skin conductance measurements). It will be appreciated that in these embodiments, the skin conductivity may or may not also be used to detect the urination events themselves. By comparing the indication of the pain, discomfort, stress, anxiety, difficulty or emotional fluctuations of the subject with indications for earlier urination events, it is possible to determine if the subject is experiencing more or less pain, discomfort, etc. during, before, and/or after urination.

In further embodiments, measurements of other physiological characteristics, such as heart rate and breathing rate, can be obtained (for example from the movement measurements) and used to determine an indication of the pain, discomfort, stress, anxiety or emotional fluctuations of the subject.

In some embodiments, a data mining approach can be used in which a classifier or model is trained to identify urination events based on several sets of movement and skin temperature measurements corresponding to known urination events. Once this classifier or model has been trained, it may be possible to identify urination events from just one of movement measurements and skin temperature measurements, or even from skin conductance measurements. For example, for a baseline period, movement measurements and skin temperature measurements are collected and urination events are identified as described above. Once data for a sufficient number of urination events is collected, models or classifiers can be trained using the data, and the model or classifier can be used to detect urination events from only the movement measurements, provided that the features of the movements before, during and after the urination events are distinctive enough from non-urination parts of the data. A similar techniques could also be used for skin temperature measurements or skin conductance measurements.

In some embodiments, since it is known that blood pressure changes during urination, blood pressure measurements of the subject can obtained, and the blood pressure measurements evaluated as part of the urination event detection.

In some embodiments, since it is known that respiration patterns change during urination, measurements of the breathing of the subject can be obtained, and the measurements of the breathing evaluated as part of the urination event detection.

In further embodiments, lifestyle patterns of the subject, such as the time that the subject wakes up, the time that the subject eats, the times that the subject sleeps, and schedule information can be used to improve urination event detection. The urination event data can be analyzed and interpreted in relation to these lifestyle patterns.

In some embodiments, the temperature of the environment (e.g. the temperature of the air in the environment) can be used to calibrate an expected change in skin temperature resulting from the urination. In particular, when skin temperature is higher, the expected decrease in skin temperature due to urination is also expected to be higher. Therefore, in some embodiments a lower bound for a predetermined range for the decrease in the skin temperature corresponding to a urination event may be increased if the skin temperature is above a threshold value.

In yet further embodiments, if information is available on the drugs or medication that the subject has taken, changes in the urination pattern of the subject or changes in characteristics of the urination events can be linked to the drugs or medication. Such information can provide more objective information about the adherence of the subject to the treatment regimen, and on whether the treatment is working.

There is therefore provided an improved method and apparatus for monitoring a subject to identify urination events of the subject.

Variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality. A single processor or other unit may fulfil the functions of several items recited in the claims. The mere fact that certain measures are recited in mutually different dependent claims does not indicate that a combination of these measures cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A method of monitoring a subject, the method comprising:
    obtaining measurements of movements of the subject over time;
    obtaining measurements of a skin temperature of an arm, wrist, hand, finger, chest or back of the subject over time; and
    processing the obtained measurements of the movements and obtained the measurements of the skin temperature to identify a urination event of the subject as a time period where a level of movement by the subject is below a threshold and the skin temperature decreases.

2. The method of claim 1, wherein the step of processing the obtained measurements comprises processing the obtained measurements of the movements to identify one or more time periods in which the level of movement is below the threshold.

3. The method of claim 1, wherein the step of processing the obtained measurements of the skin temperature comprises processing the obtained measurements to identify time periods in which the skin temperature decreases.

4. The method of claim 1, wherein the step of processing the obtained measurements of the movements further comprises:
    processing the obtained measurements of movements to detect periods of time in which the subject is walking; and
    identifying the urination event as a time period where the level of movement by the subject is below the threshold and the skin temperature decreases, and where the time period is preceded and followed by a period of time in which the subject is detected to be walking.

5. The method of claim 1, wherein the step of processing the obtained measurements of the movements further comprises:
    processing the obtained measurements of movements to detect a posture of the subject over time; and
    identifying the urination event as a time period where the level of movement by the subject is below the threshold and the skin temperature decreases, and where the subject is in a sitting or standing posture.

6. The method of claim 1, wherein the method further comprises the steps of:
    obtaining measurements of skin conductivity of the subject over time; and
    processing the obtained measurements of skin conductivity for a time period corresponding to an identified urination event to determine an indication of one or more of pain, discomfort, stress, anxiety, emotional fluctuations and/or difficulty for the subject before, during and/or after the urination event.

7. The method of claim 1, wherein the method further comprises the step of:
    analyzing one or more identified urination events to determine one or more characteristics of the urination event or events, the one or more characteristics comprising one or more of:
        a duration of the urination event;
        a time of the urination event;
        a frequency with which urination events occur; and
        an indication of pain, discomfort, stress, anxiety, emotional fluctuations and/or difficulty for the subject before, during and/or after the urination event.

8. An apparatus for monitoring a subject, the apparatus comprising:
    a processing unit configured to:
        obtain a movement signal indicative of movements of the subject over time;
        obtain a skin temperature signal indicative of skin temperature of an arm, wrist, hand, finger, chest or back of the subject over time; and
        process the movement signal and the skin temperature signal to identify a urination event by the subject as a time period where a level of movement by the subject is below a threshold and the skin temperature decreases.

9. The apparatus of claim 8, wherein the processing unit is configured to process the movement signal to identify one or more time periods in which the level of movement is below the threshold.

10. The apparatus of claim 8, wherein the processing unit is configured to process the skin temperature signal to identify time periods in which the skin temperature decreases.

11. The apparatus of claim 8, wherein the processing unit is configured to:
- process the movement signal to detect periods of time in which the subject is walking; and
- identify the urination event as a time period where a level of movement by the subject is below the threshold and the skin temperature decreases, and where the time period is preceded and followed by a period of time in which the subject is detected to be walking.

12. The apparatus of claim 8, wherein the processing unit is further configured to process the obtained measurements of the movements by:
- processing the obtained measurements of movements to detect a posture of the subject over time; and
- identifying the urination event as a time period where the level of movement by the subject is below the threshold and the skin temperature decreases, and where the subject is in a sitting or standing posture.

13. The apparatus of claim 8, wherein the apparatus further comprises one or more of:
- a movement sensor configured to measure the movements of the subject over time and output the movement signal; and
- a skin temperature sensor configured to be worn at the arm, wrist, hand, finger, chest or back of the subject, measure the skin temperature of the subject over time and output the skin temperature signal.

14. The apparatus of claim 8, wherein the apparatus further comprises a skin conductivity sensor configured to measure skin conductivity of the subject over time and output a skin conductivity signal; and wherein the processing unit is configured to process the skin conductivity signal for a time period corresponding to an identified urination event to determine an indication of one or more of pain, discomfort, stress, anxiety, emotional fluctuations and/or difficulty for the subject before, during and/or after the urination event.

15. A non-transitory computer-readable storage medium that stores machine executable instructions, which, when being executed by a processing circuit, is adapted to perform a process, the process comprising:
- obtaining measurements of movements of the subject over time;
- obtaining measurements of a skin temperature of an arm, wrist, hand, finger, chest or back of the subject over time; and
- processing the obtained measurements of the movements and obtained the measurements of the skin temperature to identify a urination event of the subject as a time period where a level of movement by the subject is below a threshold and the skin temperature decreases.

16. The non-transitory computer-readable storage medium of claim 15, wherein the processing the obtained measurements comprises processing the obtained measurements of the movements to identify one or more time periods in which the level of movement is below the threshold.

17. The non-transitory computer-readable storage medium of claim 15, wherein the processing the obtained measurements of the skin temperature comprises processing the obtained measurements to identify time periods in which the skin temperature decreases.

18. The non-transitory computer-readable storage medium of claim 15, wherein the processing the obtained measurements of the movements further comprises:
- processing the obtained measurements of movements to detect periods of time in which the subject is walking; and
- identifying the urination event as a time period where the level of movement by the subject is below the threshold and the skin temperature decreases, wherein the time period is preceded by and followed by a period of time in which the subject is detected to be walking.

19. The non-transitory computer-readable storage medium of claim 15, wherein the processing the obtained measurements of the movements further comprises:
- processing the obtained measurements of movements to detect a posture of the subject over time; and
- identifying the urination event as a time period where the level of movement by the subject is below the threshold and the skin temperature decreases, and where the subject is in a sitting or standing posture.

20. The non-transitory computer-readable storage medium of claim 15, wherein the process further comprises:
- obtaining measurements of skin conductivity of the subject over time; and
- processing the obtained measurements of skin conductivity for a time period corresponding to an identified urination event to determine an indication of one or more of pain, discomfort, stress, anxiety, emotional fluctuations and/or difficulty for the subject before, during and/or after the urination event.

21. The non-transitory computer-readable storage medium of claim 15, wherein the process further comprises:
- analyzing one or more identified urination events to determine one or more characteristics of the urination event or events, the one or more characteristics comprising one or more of:
- a duration of the urination event;
- a time of the urination event;
- a frequency with which urination events occur; and
- an indication of pain, discomfort, stress, anxiety, emotional fluctuations and/or difficulty for the subject before, during and/or after the urination event.

* * * * *